US00PP20036P2

(12) United States Plant Patent
Klemm

(10) Patent No.: US PP20,036 P2
(45) Date of Patent: May 26, 2009

(54) *PELARGONIUM* PLANT NAMED 'KLEPZ07197'

(50) Latin Name: *Pelargonium zonale*
Varietal Denomination: KLEPZ07197

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 26 days.

(21) Appl. No.: 12/077,692

(22) Filed: Mar. 20, 2008

(51) Int. Cl.
*A01H 5/00* (2006.01)

(52) U.S. Cl. ..... Plt./329

(58) Field of Classification Search ..... Plt./329
See application file for complete search history.

*Primary Examiner*—Annette H Para
(74) *Attorney, Agent, or Firm*—Jondle & Associates, P.C.

(57) ABSTRACT

A new cultivar of *Pelargonium* plant particularly characterized by an upright plant habit with good vigor and a rounded bushy plant habit, light lavender flowers with pink eyes and leaves that are tolerant to rain, is disclosed.

1 Drawing Sheet

Genus and species: *Pelargonium zonale.*
Variety denomination: 'KLEPZ07197'.

BACKGROUND OF THE NEW PLANT

The present invention comprises a new and distinct cultivar of *Pelargonium,* botanically known as *Pelargonium zonale,* and hereinafter referred to by the cultivar name 'KLEPZ07197'. 'KLEPZ07197' was discovered as a seedling resulting from a cross in July 2002 in Stuttgart, Germany between the proprietary female *Pelargonium* parent, 'KLEP01012' (U.S. Plant Pat. No. 13,743) and the proprietary male *Pelargonium* plant, 'klesail' (unpatented). A single plant selection was subsequently chosen for further evaluation and for asexual propagation.

The new cultivar was created in 2002 in Stuttgart, Germany and has been asexually reproduced repeatedly by vegetative cuttings in Stuttgart, Germany over a 4 and one-half-year period. 'KLEPZ07197' has been found to retain its distinctive characteristics through successive asexual propagations.

Plant Breeder's Rights for this cultivar were applied for in Switzerland on Apr. 23, 2007 and in Canada on Mar. 30, 2007. 'KLEPZ07197' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. An upright plant habit, with good vigor and a rounded, bushy plant habit;
2. Light lavender flowers with pink eyes; and
3. Leaves that are tolerant to rain.

DESCRIPTION OF THE PHOTOGRAPH

This new *Pelargonium* plant is illustrated by the accompanying photograph which shows blooms, buds, and foliage of the plant; the colors shown are as true as can be reasonably obtained by conventional photographic procedures. The photograph is of a plant about 3-months old and grown from rooted cuttings in a 12-cm pot under greenhouse (glasshouse) in Stuttgart, Germany under conditions which approximate those generally used in commercial practice.

DESCRIPTION OF THE NEW CULTIVAR

The following detailed descriptions set forth the distinctive characteristics of 'KLEPZ07197'. The data which defines these characteristics were collected from asexual reproductions carried out in Stuttgart, Germany. The plant history was taken on 3-month old, un-pinched plants in 12-cm pots in a greenhouse in January through April. The color readings were determined under natural light. Color references are to the R.H.S. Colour Chart of The Royal Horticultural Society of London (R.H.S.) (2001).

DETAILED BOTANICAL DESCRIPTION

Classification:
- *Family.*—Geraniacaea.
- *Species.*—*Pelargonium zonale.*
- *Common name.*—*Pelargonium* (Geranium), zonal geranium.
- *Denomination.*—'KLEPZ07197'.

Parentage:
- *Female parent.*—The proprietary female *Pelargonium* parent, 'KLEP01012' (U.S. Plant Pat. No. 13,743).
- *Male parent.*—The proprietary male *Pelargonium* parent, 'klesail' (unpatented).

Plant:
- *Habit.*—Upright.
- *Height.*—28 cm to 34 cm.
- *Spread.*—30 cm.
- *Life cycle.*—Perennial, but usually treated as an annual.
- *Form.*—Rounded, bushy.
- *Time to produce a rooted cutting.*—16 to 18 days.
- *Time to bloom from propagation.*—Approximately 80 days.

Stems:
- *Stem color.*—RHS 137D.
- *Pubescence.*—Present.
- *Stem form.*—Round.

*Diameter.*—0.5 cm to 1.4 cm.
*Length.*—6.0 cm to 17.0 cm.
*Internode length.*—0.8 cm to 1.5 cm.

Leaves:
*Arrangement.*—Alternate.
*Shape.*—Typical of geraniums, kidney-shaped.
*Apex.*—Rounded.
*Base.*—Open.
*Margin.*—Crenate.
*Surface texture* (*both sides*).—Dull with very short pubescence.
*Length.*—6.0 cm to 8.0 cm.
*Width.*—8.0 cm to 9.0 cm.
*Color.*—Upper surface: RHS 137A. Lower surface: RHS 137C.
*Petiole.*—Length: 5.0 cm. Diameter: 0.15 cm to 0.2 cm. Color: RHS 137C. Texture: Rough, slightly pubescent.
*Venation pattern.*—Palmate.
*Venation color.*—RHS 137C.
*Zonation.*—Absent.

Inflorescence:
*Flowering habit.*—Continuous.
*Lastingness of inflorescence on the plant.*—15 days.
*Umbels.*—Length: 6.0 cm to 8.0 cm. Diameter: 12.0 cm.
*Individual florets of the umbel.*—Depth: 1.0 cm to 2.0 cm. Diameter: 4.5 cm.
*Fragrance.*—Absent.

Flower buds:
*Cluster shape.*—Umbelliferous.
*Length.*—0.5 cm to 1.2 cm.
*Width.*—0.3 cm to 0.6 cm.
*Texture.*—Rough.
*Bud.*—Shape: Elliptical. Apex: Acute. Base: Obtuse. Margin: Entire, smooth. Color: RHS 137C.

Petals:
*Quantity per flower.*—6 to 8.
*Shape.*—Rounded.
*Apex.*—Rounded.
*Base.*—Attenuate.
*Margin.*—Entire.
*Length.*—2.2 cm.
*Width.*—1.8 cm.
*Color of lobes.*—Upper lobes: Upper surface: Main color is RHS 76B with an RHS 74B eye. Lower surface: RHS 76D. Lower lobes: Upper surface: Main color is RHS 76B with an RHS 74B eye. Lower surface: RHS 76D.

Sepals:
*Number per flower.*—5.
*Shape.*—Elliptic.
*Apex.*—Acute.
*Base.*—Obtuse.
*Margin.*—Entire.
*Color* (*both surfaces*).—RHS 137C.
*Length.*—0.8 cm to 1.2 cm.
*Width.*—0.5 cm to 0.8 cm.

Pedicel:
*Length.*—2.0 cm to 2.5 cm.
*Diameter.*—0.1 cm to 0.2 cm.
*Color.*—RHS 137C.
*Texture.*—Rough.

Peduncle:
*Length.*—12.0 cm to 17.0 cm.
*Diameter.*—0.5 cm to 0.6 cm.
*Color.*—RHS 137C.
*Texture.*—Rough.

Reproductive organs:
*Stamens.*—Anther length: 0.3 cm. Filament length: 0.6 cm. Filament color: RHS 65C. Pollen amount: Moderate. Pollen color: RHS 33B.
*Pistils.*—Number: 1. Stigma color: RHS 74C. Style length: 0.5 cm. Style color: RHS 155D. Ovary arrangement: Club-shaped.

Fruit/seed set: None observed.

Disease and insect resistance: No particular disease or insect resistance noted.

COMPARISON WITH PARENTAL AND COMMERCIAL CULTIVARS

'KLEPZ07197' differs from the female parent, the proprietary female *Pelargonium* parent, 'KLEP01012' (U.S. Plant Pat. No. 13,743) in that 'KLEPZ07197' has green leaves and lavender flowers with pink eyes, while 'KLEP01012' has darker green leaves and purple and light-pink bi-colored flowers. Additionally, 'KLEPZ07197' has a more vigorous growth habit than 'KLEP01012'.

'KLEPZ07197' differs from the male parent, the proprietary *Pelargonium* plant 'klesail' (unpatented) in that 'KLEPZ07197' has green leaves and lavender flowers with dark pink eyes, while 'klesail' has darker green leaves and white flowers.

'KLEPZ07197' differs from the commercial comparison variety 'klegrato' (unpatented and also known as 'katinka') in that 'KLEPZ07197' has a lighter flower color, better branching and a more vigorous growth habit than 'klegrato'.

'KLEPZ07197' differs from the commercial comparison variety 'klekit' (unpatented and also known as 'kitty') in that 'KLEPZ07197' has lavender flowers with pink eyes, while 'klekit' has lavender flowers with purple eyes. Additionally, 'KLEPZ07197' has lighter green leaves and a more vigorous growth habit than 'klekit'.

I claim:

1. A new and distinct cultivar of *Pelargonium* plant as shown and described herein.

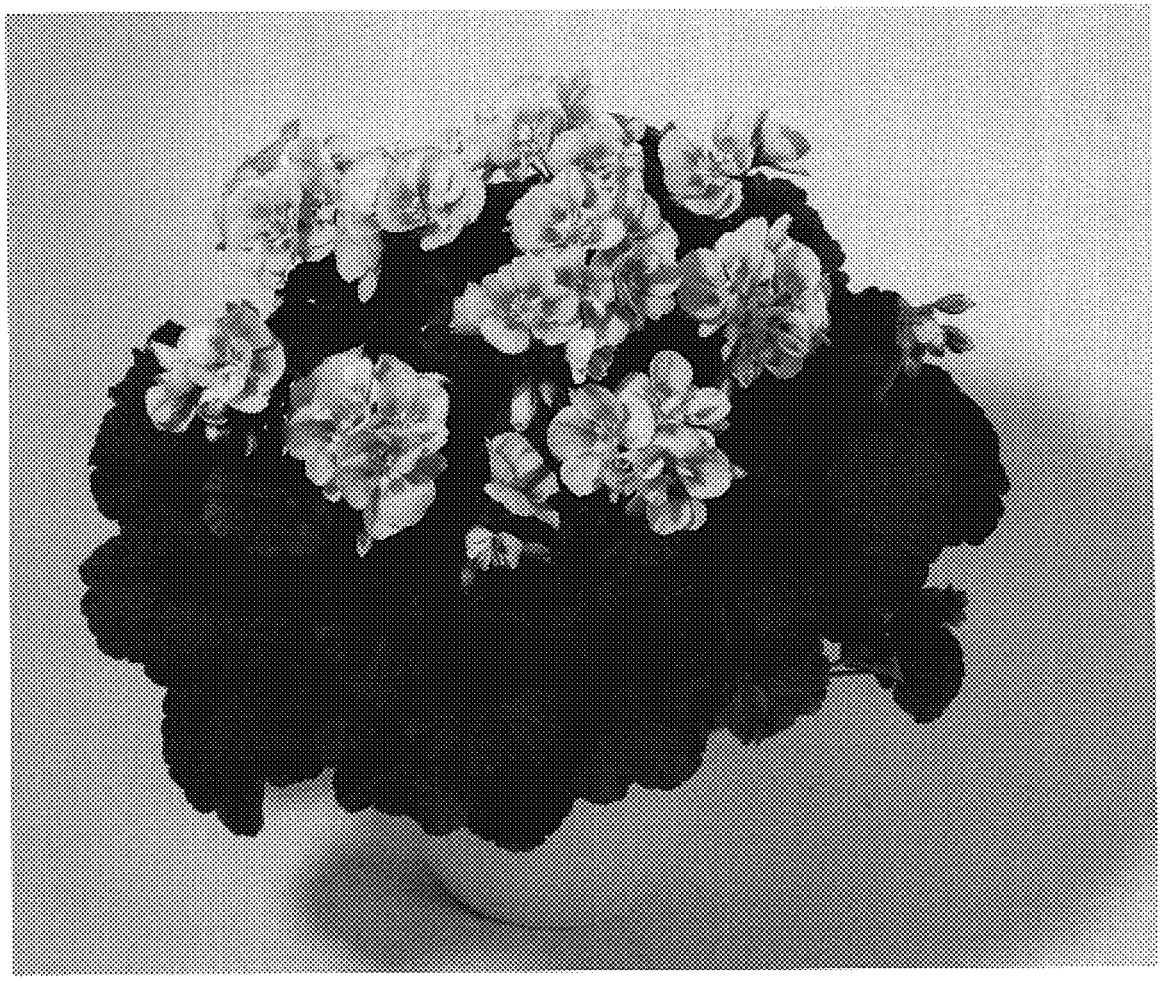

* * * * *